US008229064B2

(12) United States Patent  
Grodzins

(10) Patent No.: US 8,229,064 B2
(45) Date of Patent: Jul. 24, 2012

(54) LOCALIZATION OF AN ELEMENT OF INTEREST BY XRF ANALYSIS OF DIFFERENT INSPECTION VOLUMES

(75) Inventor: Lee Grodzins, Lexington, MA (US)

(73) Assignee: Thermo Scientific Portable Analytical Instruments Inc., Tewksbury, MA (US)

( * ) Notice: Subject to any disclaimer, the term of this patent is extended or adjusted under 35 U.S.C. 154(b) by 277 days.

(21) Appl. No.: 12/771,646

(22) Filed: Apr. 30, 2010

(65) Prior Publication Data

US 2010/0278303 A1  Nov. 4, 2010

Related U.S. Application Data

(60) Provisional application No. 61/174,426, filed on Apr. 30, 2009.

(51) Int. Cl.
*G01N 23/223* (2006.01)
(52) U.S. Cl. ............................................. 378/45; 378/44
(58) Field of Classification Search .............. 378/44–50
See application file for complete search history.

(56) References Cited

U.S. PATENT DOCUMENTS

| 5,457,725 | A | 10/1995 | Sato |
| 6,453,002 | B1 | 9/2002 | Mazor et al. |
| 7,420,163 | B2 | 9/2008 | Schueler |
| 2007/0092060 | A1* | 4/2007 | Grodzins ..................... 378/50 |
| 2008/0049895 | A1 | 2/2008 | Agnihotri et al. |
| 2008/0192897 | A1 | 8/2008 | Piorek et al. |
| 2009/0067572 | A1 | 3/2009 | Grodzins et al. |
| 2009/0074137 | A1* | 3/2009 | Agnihotri et al. ............ 378/50 |
| 2010/0189215 | A1* | 7/2010 | Grodzins et al. ............ 378/45 |

* cited by examiner

*Primary Examiner* — Hoon Song
(74) *Attorney, Agent, or Firm* — Gordon Stewart

(57) ABSTRACT

An apparatus and method are disclosed for localizing an element of interest in a sample by comparing XRF spectra acquired from at least two distinct but overlapping inspection volumes. The inspection volumes are varied by changing the geometry of the exciting x-ray and/or fluoresced x-ray beam(s), which may be accomplished by repositioning multi-apertured collimators. Comparison of the XRF spectra acquired from different inspection volumes provides an indication as to whether the element of interest (e.g., lead) is present in a coating layer, in the underlying bulk material, or in both.

12 Claims, 5 Drawing Sheets

LOCALIZATION OF AN ELEMENT OF INTEREST BY XRF ANALYSIS OF DIFFERENT INSPECTION VOLUMES

CROSS-REFERENCE TO RELATED APPLICATION

This application claims the priority benefit under 35 U.S.C. §119(e) of U.S. Provisional Patent Application Ser. No. 61/174,426 entitled "Localization of an Element of Interest by XRF Analysis of Different Inspection Volumes", filed on Apr. 30, 2009, the entire disclosure of which is incorporated herein by reference.

FIELD OF THE INVENTION

The present invention relates generally to the measurement of elemental composition by x-ray fluorescence (XRF), and more particularly to a method and apparatus for identifying the location of an element of interest, such as lead, in a sample by differential measurement of the intensities of characteristic fluorescent x-rays.

BACKGROUND OF THE INVENTION

XRF is a reliable, sensitive and widely used technique for the detection and quantification of elements of interest in various sample types. In XRF analysis, a radioisotope source or x-ray tube generates a beam of exciting radiation which is directed onto a sample. Elements in the sample responsively emit fluorescent x-rays of characteristic energies. The emitted x-rays are sensed by a detector, which produces signals representative of the energies of the received x-rays. These signals are processed to construct a spectrum of x-ray count rate as a function of energy. The concentration of an element of interest, such as lead, may be determined from the intensity of its characteristic peak(s) in the spectrum.

One growing application of XRF analysis is the screening of consumer goods, such as toys, for the presence of lead and other hazardous elements at unacceptably high concentrations. Consumer goods are typically of heterogeneous construction, having multiple layers of material of varying thicknesses, and an instrument operator will often have little or no information regarding the specific construction of an inspected object at the time of testing. However, it may be desirable or necessary to identify the location within the inspected object of the detected element of interest e.g., whether the element is located in a coating layer or in the underlying substrate. Toys, for example, will generally have a thin layer of paint or other coating overlying a bulk material. If lead is detected in the toy, it may be important to discern whether the lead is present primarily in the paint or primarily distributed through the bulk material, since the applicable regulatory standard and optimal method for calculating the lead concentration can depend on the location of the lead.

The location of a detected element of interest may be determined by examining the intensity ratio of two characteristic x-ray lines corresponding to the element of interest (e.g., the $L_\alpha$ and $L_\beta$ x-rays of lead), one of which is preferentially absorbed relative to the other (see, for example, U.S. Patent Application Publication No. 2009/0067572 by Grodzins et al.) This approach, while providing satisfactory results for certain applications, may not be suitable for a broader range of elements of interest and sample matrices. For example, it may be difficult to distinguish coating lead from bulk lead in thin, low-density materials such as polyethylene. Furthermore, the intensity ratio method cannot be employed, except in special cases, to elements whose concentration is measured by the intensity of the K x-rays.

Thus, there remains a need in the art for localization technique that may be successfully and reliably employed for XRF analysis of a variety of elements of interest in disparate types of samples.

SUMMARY OF THE INVENTION

Roughly described, an element of interest is localized in a sample by XRF analysis by irradiating the sample with exciting radiation and detecting characteristic x-rays emitted from at least two overlapping but distinct inspection volumes. The inspection volumes may be controllably changed by varying the collimation of the exciting and/or fluoresced x-rays (e.g., by moving one or more collimator structures), or by partially blocking the exciting and/or fluoresced x-rays (e.g., by positioning an eclipser structure). According to one implementation, the inspection volumes include a first inspection volume that extends to both the coating layer and the bulk of the sample, and a second inspection volume that includes only the bulk of the sample. By comparing the intensities of the characteristic x-rays emitted from the different inspection volumes, the location of the element of interest (e.g., in the coating, bulk or both) may be determined.

DETAILED DESCRIPTION OF EMBODIMENTS

Figure 1:
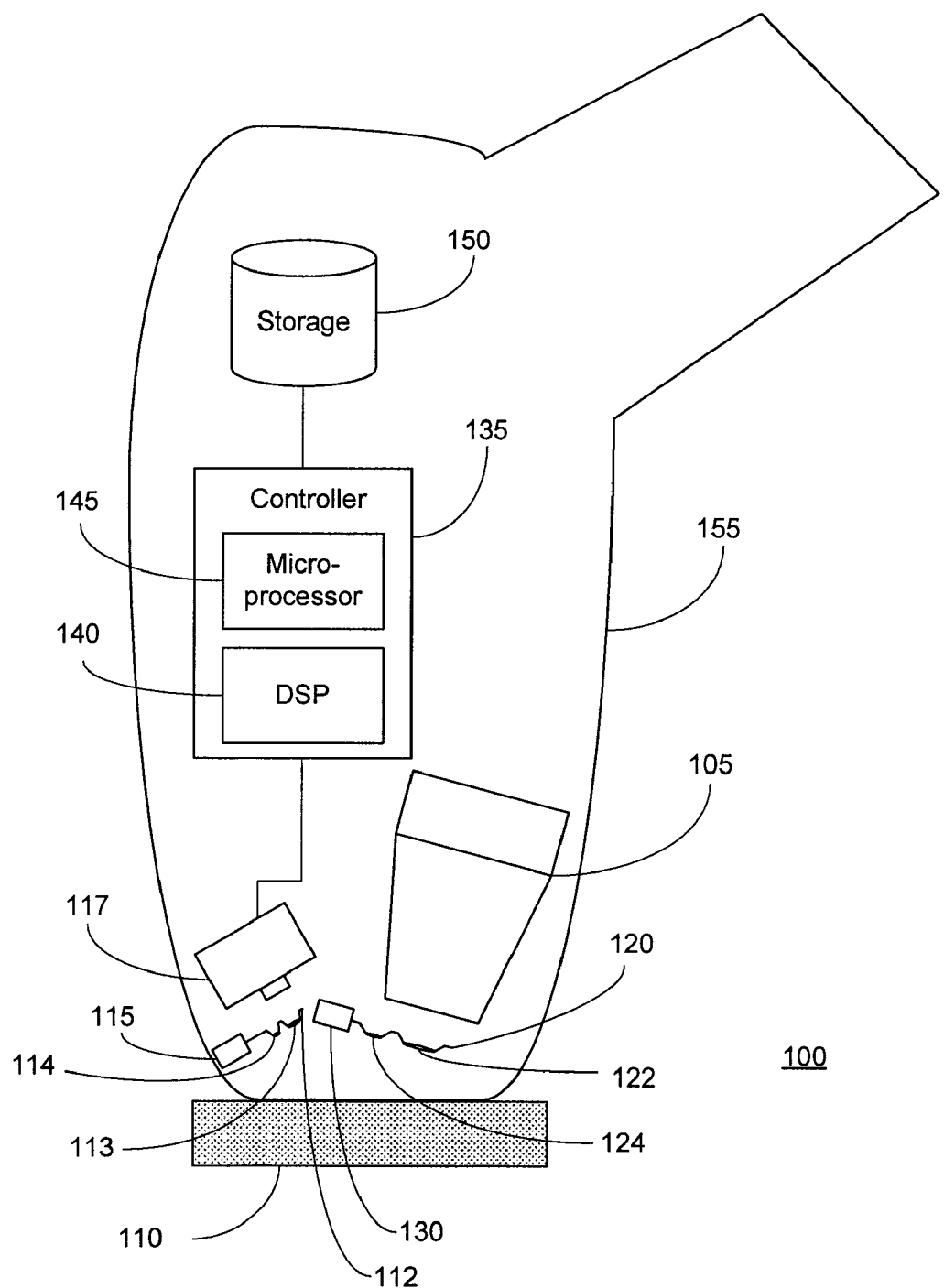
FIG. 1 is a symbolic diagram of an XRF analyzer adapted to change inspection volumes, in accordance with an illustrative embodiment of the invention.

FIG. 1 is a symbolic diagram of the components of an XRF analyzer 100 specially adapted to change inspection volumes in order to localize an element of interest by comparison of XRF spectra. XRF analyzer 100 includes an x-ray source 105 for generating a primary radiation beam to excite lead atoms in sample 110. X-ray source 105 may take the form of any suitable x-ray tube or radioisotope source. As used herein, the term "x-ray" is broadly defined to include any radiation having an energy suitable for causing fluorescence of the element of interest via ejection of an inner shell electron, and may encompass radiation classified as gamma-rays in other contexts. A movable collimator 112 is positioned in the path of the primary x-rays (also referred to as exciting x-rays) to define the geometry of the primary beam incident on sample 110. As is discussed in further detail below, collimator 112 may be adapted with at least two apertures 113 and 114 of differing size and/or shape. An actuator 115, in mechanical association with collimator 112, selectably aligns one of the two apertures 113 and 114 with the x-ray beam emitted by source 105, such that the beam collimation is fixed by selection of the appropriate aperture. As is described in U.S. Patent Application Publication No. 2008/0192897 by Piorek et al., movement of collimator 112 may be effected by means of a pinion gear driven by actuator 115, which engages a corresponding rack gear formed on collimator 112. In alternative embodiments, collimator 112 may have a single aperture, and the desired variation of the beam collimation may be achieved by moving the collimator toward or away from source 105.

Detector 117 is positioned to receive radiation emitted by sample 110. The emitted radiation will typically comprise a mixture of fluorescent x-rays characteristic of specific elements in sample 110 and elastically scattered (Rayleigh) and inelastically scattered (Compton) x-rays. The design and operation of XRF detectors are well known in the art and hence will not be discussed herein. Generally described, detector 117 generates a signal pulse in response to reception of an x-ray photon, the size of the pulse being representative of the photon's energy. Detector 117 may incorporate or have associated therewith preamplifier circuitry for integrating and amplifying current produced by the detector 117 crystal. In various implementations, detector 117 may take the form of a silicon PIN detector, cadmium telluride detector, or silicon drift detector.

Another collimator 120 is positioned in the path of the fluoresced x-rays to adjustably control the geometry of the beam conveyed to and sensed by detector 117. Collimator 120 is adapted with at least two differently sized apertures 122 and 124, a selected one of which is aligned with the optical axis of detector 117. The selection of aperture 122 or 124 for alignment with detector 117 is accomplished by operation of actuator 130, which (as described above in connection with exciting beam collimator 112) drives a pinion gear engaged with a rack gear formed on collimator 120.

The sizes and positioning of source 105, detector 117, and collimators 112 and 120 are selected to produce desired inspection volume geometries, as will be discussed below. In the example of an analyzer configured to localize an element of interest in a painted or otherwise coated object, the sizes and positions of these components are chosen to produce a set of inspection volumes, whereby one of the inspection volumes encompasses only the bulk portion of the object, and the other inspection volume extends to both the paint layers and the bulk portion.

The output of detector 117 is conveyed to programmable controller 135, which will typically incorporate at least one digital signal processor (DSP) 140 configured to amplify, process and accumulate the signal pulses such that an energy spectrum of the detected radiation may be constructed. As is known in the art, DSP 140 may execute routines for attenuating signals generated by detector 117 arising from various sources of noise. Programmable controller 135 may also include a specialized or general purpose microprocessor 145 for executing program instructions relating to data acquisition and analysis and instrument control, including implementations of the method steps depicted in FIG. 2 and discussed below. The program instructions executed by DSP 140 and microprocessor 145 may be stored in hardware, firmware or software logic form within controller 135 and/or non-volatile storage 150 coupled to controller 125. Storage 150 may also hold test results and information input by the operator.

The various components of XRF analyzer 100 may be located within a common housing 155 designed to be hand-held by the operator. A touch screen display (not depicted) may be incorporated into or mounted to housing 155 to present text and graphics (e.g., representing analysis results) and to accept operator input. XRF analyzer 100 will typically include a wired (e.g., USB) or wireless (e.g., 802.11g) communications port to enable the uploading and downloading of analysis results, software, and other information to and form an external computer. In alternative implementations, certain of the components of XRF analyzer 100 may be located remotely from each other, e.g., components of controller 135 may reside on a general purpose computer that communicates with the other components over a wired or wireless connection.

Figure 2:
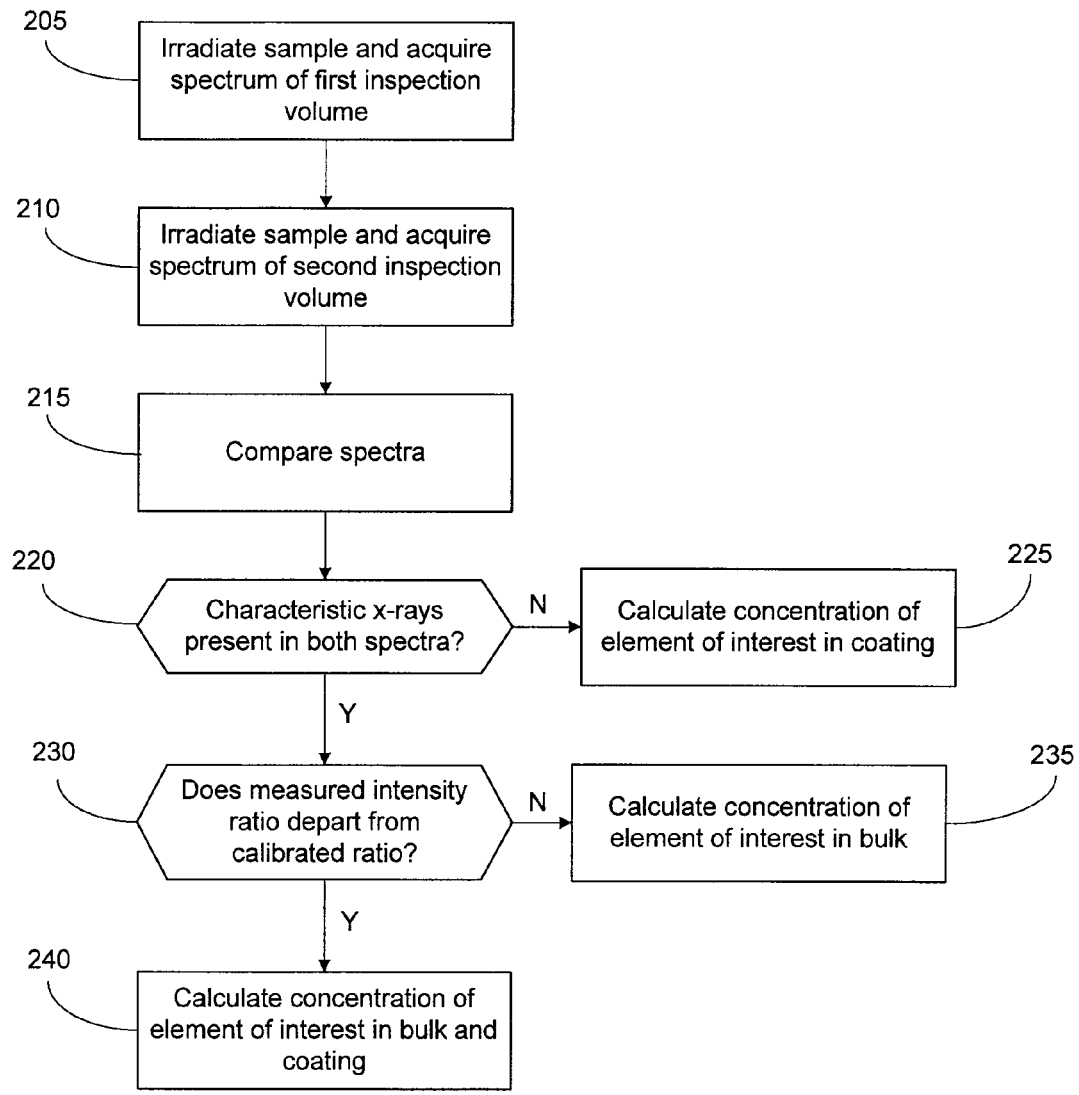
FIG. 2 is a flowchart depicting the steps of a method for localizing an element of interest by comparing XRF spectra acquired in overlapping inspection volumes.

FIG. 2 shows the steps of a method for operating an XRF instrument, such as XRF analyzer 100, to determine the location of an element of interest within an inspected sample by comparing results acquired from different inspection volumes. It should be noted that although the steps are presented in a particular order in the flowchart, certain of the steps may be conducted concurrently rather than sequentially, and so the flowchart should not be regarded as imposing a specifically ordered sequence of steps.

In step 205, a beam of primary x-ray radiation is directed unto the sample, e.g., by operation of x-ray source 105. This step may be initiated by operator action, such as by depressing a trigger mounted to housing 155. The operation of x-ray source 105 is preferably directed by controller 135, and certain of the beam parameters, such as intensity and energy, may be selected or adjusted based on operator input, for example by specifying the class or type of material.

Figure 3A:
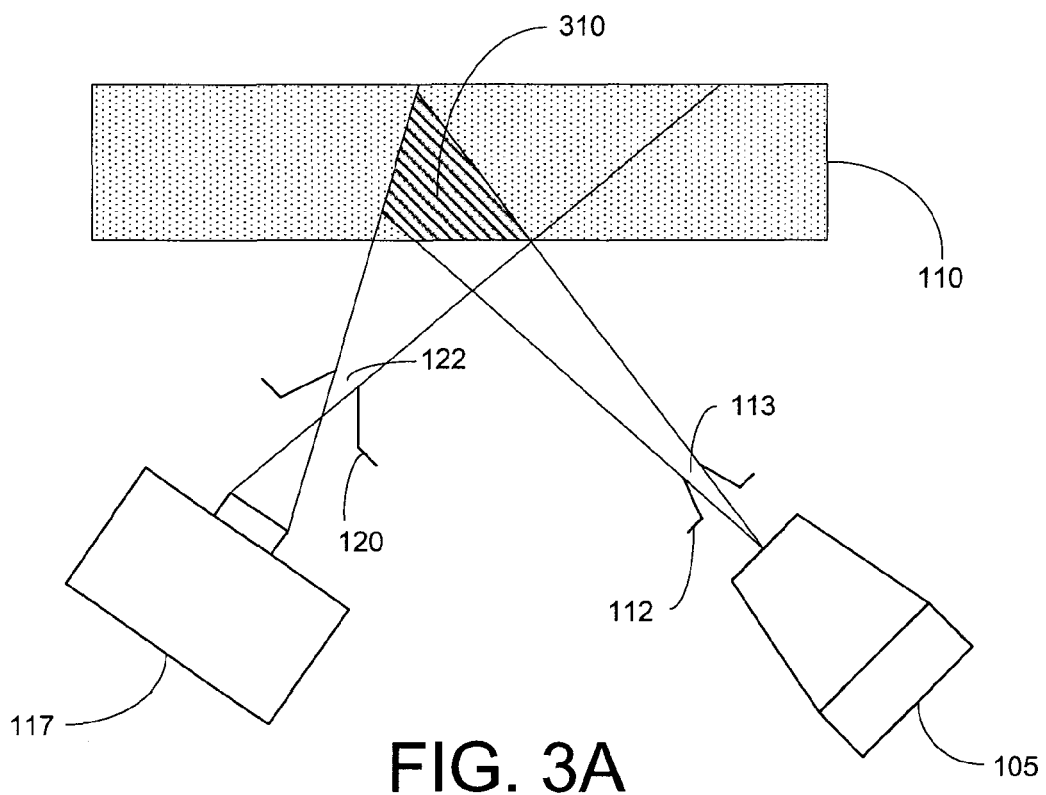
FIGS. 3A and 3B are fragmentary diagrams of the XRF analyzer of FIG. 1, showing how different inspection volumes are defined in a generic sample by varying the collimation of the exciting and fluoresced x-ray beams.
Figure 4A:
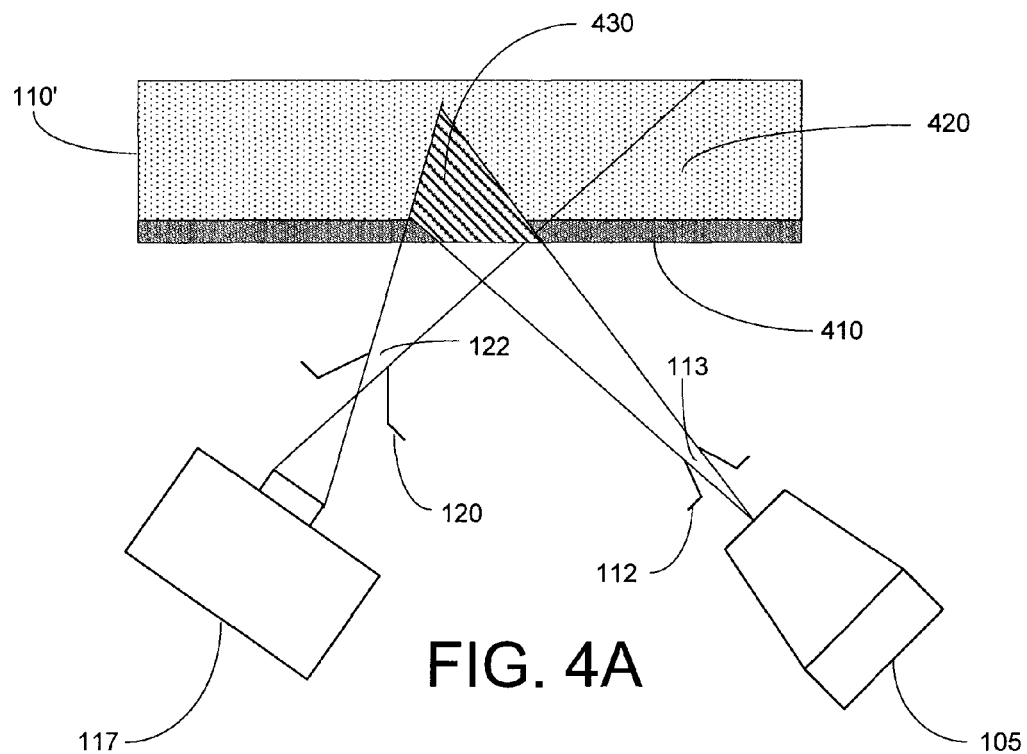
FIGS. 4A and 4B are fragmentary diagrams of the XRF analyzer of FIG. 1, showing different inspection volumes defined in a particular sample having a thin coating layer overlying a bulk material.
Figure 4B:
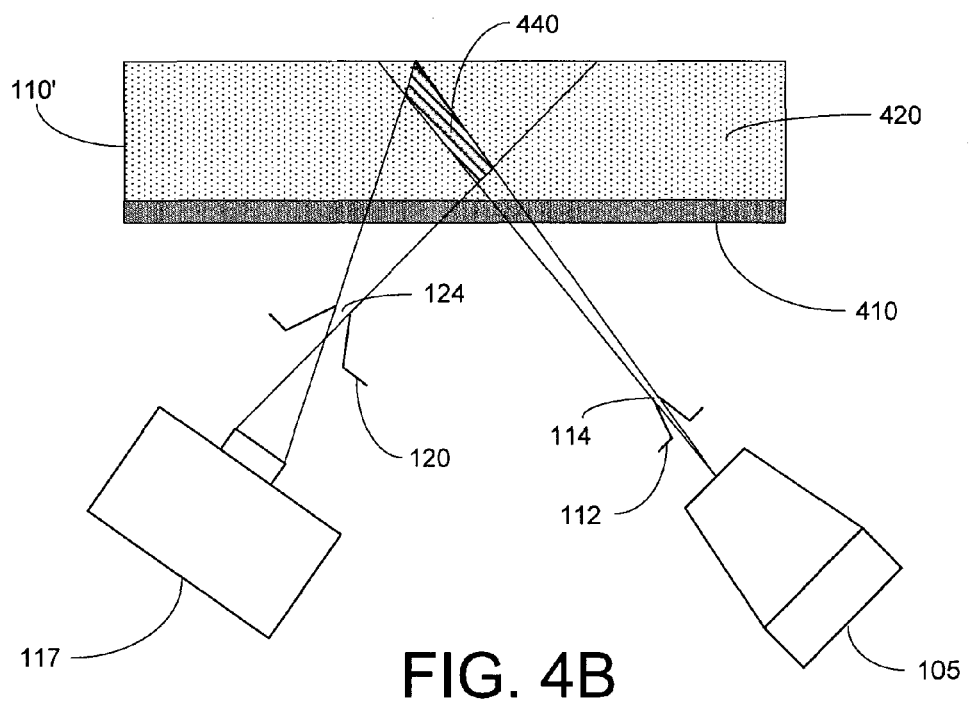

For the duration of step 205, exciting beam collimator 112 and fluoresced beam collimator 120 are set in their first positions, as shown in FIG. 3A. It will be appreciated that certain components of analyzer 100 have been omitted from FIG. 3A for the purpose of clarity. For an analyzer 100 of the handheld type, the operator holds analyzer 100 such that its front face (not depicted), which is provided with windows through which the exciting and fluoresced x-rays are transmitted, abuts a surface of sample 110. This action fixes the positioning of source 105 and detector 117 relative to sample 110. Other techniques (e.g., use of a frame which receives and holds both the analyzer and sample) may be employed to fix the relative positioning of the analyzer components and sample. In their first positions, exciting beam collimator 112 and fluoresced beam collimator 120 have their first, larger apertures 113 and 122 aligned with the respective optical axes of source 105 and detector 117. The intersection of the resultant exciting and fluoresced x-ray beams defines a first inspection volume 310 within sample 110. First inspection volume 310 constitutes the portion of sample 110 which is irradiated by exciting x-rays and "viewed" by detector 117, and represents the region for which the x-ray spectrum is acquired during step 205. It may be discerned that first inspection volume 310 encompasses both the region directly underlying the surface of sample 110 and the region extending more deeply into the thickness of sample 110. As will be discussed in more detail below in connection with FIGS. 4A and 4B, a spectrum acquired from this inspection volume would contain information about the elemental composition of a coating (e.g., paint) layer and the bulk material supporting the coating layer.

During step 205, controller 135 receives pulses generated by detector 117, and DSP 140 processes and accumulates the pulses over an analysis time to construct a first energy spectrum, from which the intensities of the various x-ray peaks of interest may be determined. The total analysis time, i.e., the period over which the sample is irradiated and the emitted radiation is detected and processed, may be controlled by the operator, set to a fixed value, or may be adjusted based on evaluation of the energy spectrum as it is acquired (e.g., terminating the analysis when a specified number of counts have been detected, or when a targeted signal-to-noise ratio has been achieved). A representation of the energy spectrum acquired during step 205 (referred to herein as the first energy spectrum) may be stored in storage 150 for use in the subsequent comparison step 215.

Figure 3B:
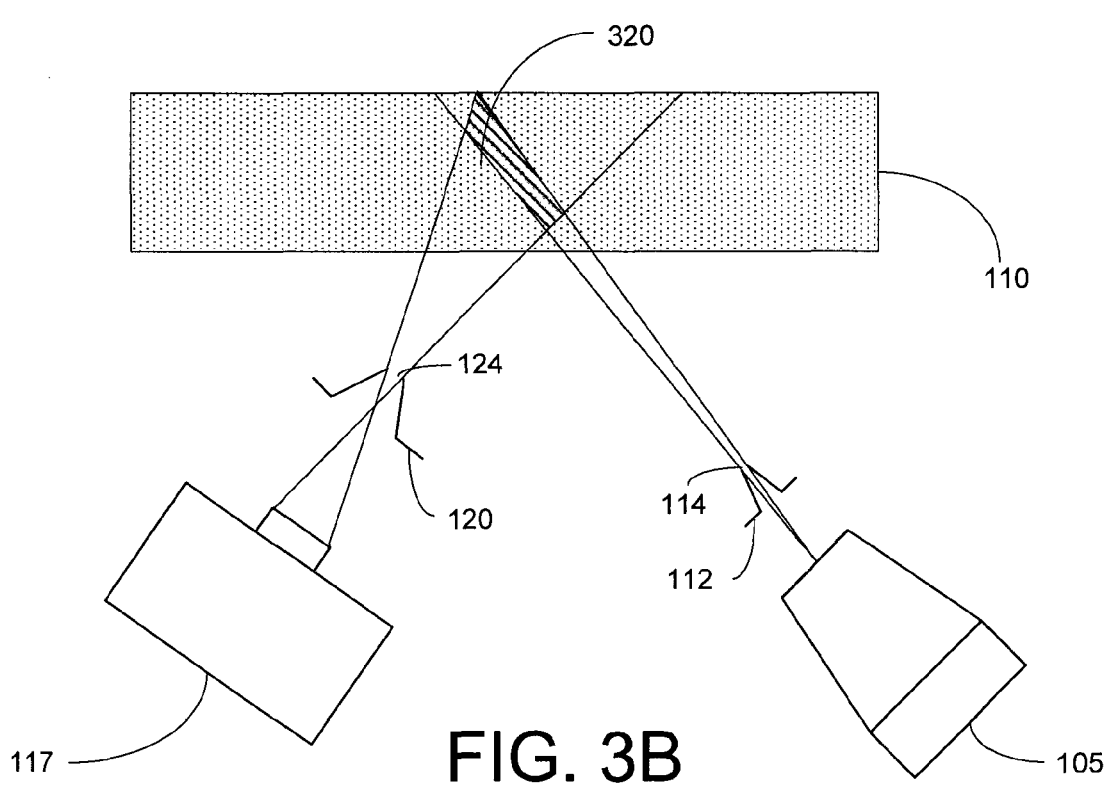

Next, in step 210 the geometry of the exciting and fluoresced x-ray beams are changed by moving collimators 112 and 120 to their second positions, such that second, smaller, apertures 114 and 124 are aligned with the respective optical axes of source 105 and detector 117, and a second energy spectrum is acquired of radiation emitted from a second inspection volume 320. FIG. 3B depicts collimators 112 and 120 in their second positions. Switching of the collimators' positions is preferably effected under automated control, although certain implementations may utilize manual switching initiated by the operator. The resultant second inspection volume 320, shown in FIG. 3B, overlaps with but is non-identical to first inspection volume 310. In contradistinction to first inspection volume 310, second inspection volume 320 does not encompass the region of sample 110 immediately adjacent to its surface, but instead covers only a more deeply buried portion of the sample. Thus, the spectrum acquired of second inspection volume 320 will contain information only about the elemental composition of the underlying bulk material.

As in step 205, controller 135 receives pulses generated by detector 117, and DSP 140 processes and accumulates the pulses over an analysis time to construct a second energy spectrum, from which the intensities of the various x-ray peaks of interest may be determined. A representation of the second energy spectrum acquired during step 210 may be stored in storage 150.

The first energy spectrum is then compared to the second energy spectrum, step 215, to ascertain whether fluoresced radiation characteristic of one or more elements of interest is present in only one of the spectra or in both spectra. In an illustrative example, the element of interest in lead, which emits characteristic $L_\alpha$ and $L_\beta$ x-rays at 10.5 and 12.6 keV, respectively. Assuming that lead is present somewhere in the sample, the first energy spectrum will exhibit peaks at the $L_\alpha$ and $L_\beta$ energies. The second energy spectrum may or may not exhibit peaks at the characteristic energies. If it is determined (step 220) that the characteristic peaks are absent from the second energy spectrum, then it may be inferred that the lead (or other element of interest) is localized in the region of sample 110 directly underlying its surface, which region is outside of second inspection volume 320. The significance of this result may be more readily understood with reference to FIGS. 4A and 4B, which substitute a painted (or otherwise coated) sample 110' for generic sample 100 depicted in FIGS. 3A and 3B. Sample 110' is composed of a thin coating layer 410 overlying a relatively thick bulk material 420. It may be discerned that first inspection volume 430 (shown in FIG. 4A) extends to portions of both coating layer 410 and bulk 420, whereas second inspection volume 440 (shown in FIG. 4B) is limited to a portion of bulk 420 and excludes coating layer 410. If the element of interest is present only in coating layer 410, then characteristic fluoresced x-rays of the element of interest (e.g., the $L_\alpha$ and $L_\beta$ x-rays of lead) are observed in the first energy spectrum (acquired from first inspection volume 430), but not in the second energy spectrum (acquired from second inspection volume 440). If it is determined that the element of interest is present only in the coating layer, then the concentration of the element of interest may then be determined from the measured intensity of the characteristic x-rays in the first spectrum, for example by an empirical method utilizing a stored calibration curve of measured characteristic x-ray intensity(ies) versus concentration derived from measurements of painted or coated reference samples, step 225. Those skilled in the art will recognize that the intensity of the characteristic x-rays may be calculated by integration of the corresponding peak in the energy spectrum.

If peaks of the characteristic radiation of the element of interest are identified in both the first and second spectra, then two possibilities exist: the element of interest may be present only in bulk 420, or in both bulk 420 and coating layer 410. To distinguish between these two possibilities, the intensity ratio of the characteristic x-rays (e.g., the ratio of the measured intensity of the $L_\alpha$ and $L_\beta$ x-rays of lead, or their sum, in the first spectrum to the measured intensity of the corresponding x-rays in the second spectrum) may be compared to a stored calibrated intensity ratio that is empirically derived by acquisition of spectra from a homogeneous (i.e., uncoated) reference sample, step 230. If the measured intensity ratio corresponds to the calibrated intensity ratio, then it may be inferred that the element of interest is present only in bulk 420. If it is determined that the element of interest is present only in the bulk, then the concentration of the element of interest may then be determined from the measured intensity of the characteristic x-rays in either the first or second spectra, for example by an empirical method utilizing a stored calibration curve of measured characteristic x-ray intensity(ies) versus concentration derived from measurements of reference samples, step 235.

In the event that the measured intensity ratio departs substantially from the calibrated intensity ratio, it may be concluded that the element of interest is present both in bulk 420 and coating layer 410. The concentration of the element of interest in bulk 420 may then be determined from the intensity of the characteristic x-rays in the second energy spectrum (employing, for example, a stored empirically derived calibration curve), and the concentration of the element of interest in coating layer 410 may be determined from the intensities of the characteristic x-rays in the first and second energy spectra, using a full calibration of analyzer 100, step 240.

Those skilled in the art will recognize that the apparatus and method described above may be readily adapted to produce and acquire spectra from three or more overlapping inspection volumes. Furthermore, while embodiments of the invention have been depicted and described herein with respect to the localization of an element of interest in the coating layer or bulk, the invention may also be employed for the measurement of the homogeneity of the concentration of one or more elements of interest in uncoated materials. In such an application, a collimator may be designed to illuminate different portions of the sample as the collimator scans continuously or stepwise across the exciting and/or fluoresced x-ray beams.

Figure 5A:
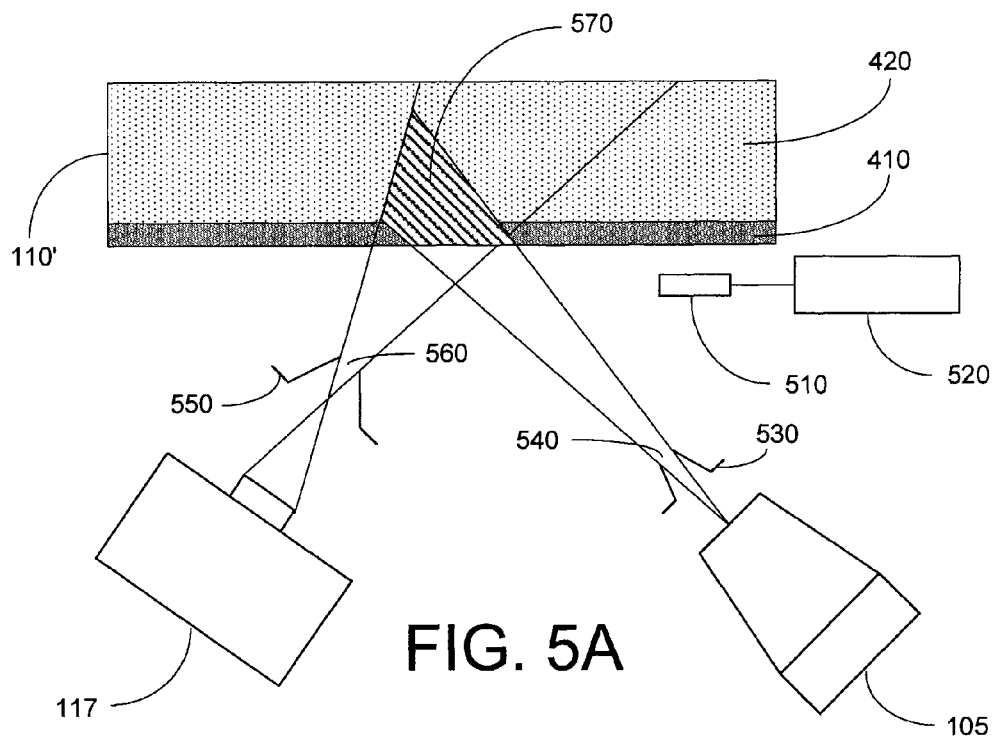
FIGS. 5A and 5B are fragmentary diagrams of an XRF analyzer of alternative design showing how different inspection volumes are defined in a sample by selectively blocking a portion of the exciting and fluoresced x-ray beams.
Figure 5B:
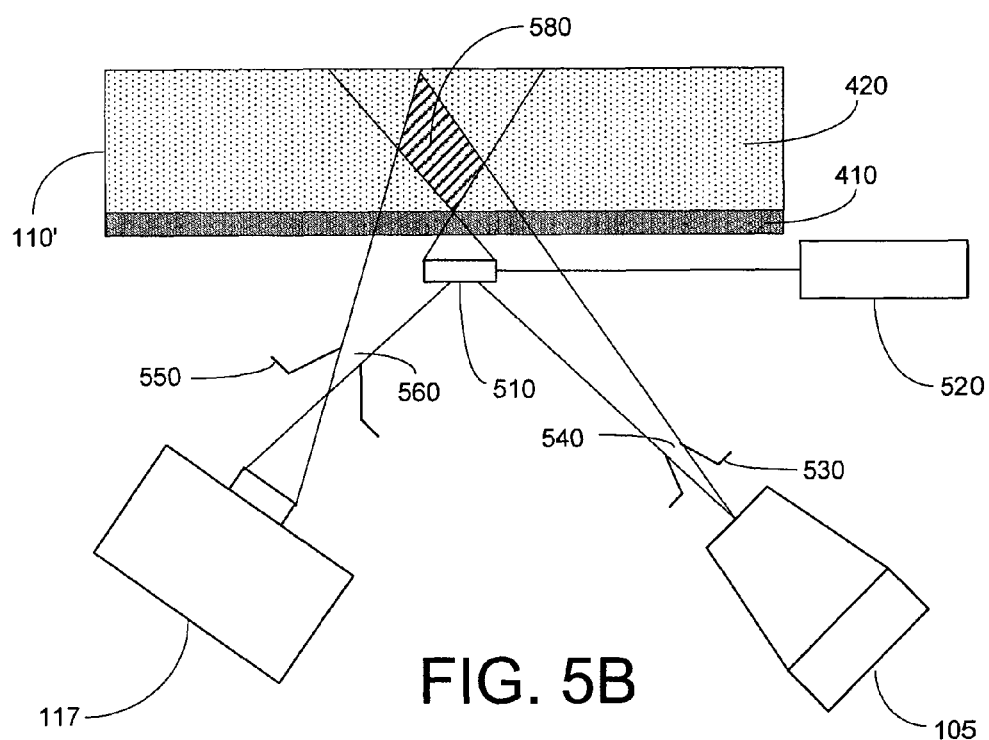

FIGS. 5A and 5B depict an alternative design of the XRF analyzer, wherein different inspection volumes are defined in sample 110' by moving an eclipser 510, as effected by operation of actuator 520, to selectively block a portion of the exciting and fluoresced x-rays. Fixed collimators 530 and 550, having respective apertures 540 and 560, may be utilized to tailor the geometry of the exciting x-ray beam directed onto sample 110' and the fluoresced x-ray beam delivered to detector 117. In FIG. 5A, eclipser 510 is displaced from the exciting and fluoresced x-rays. First inspection volume 570, defined by the intersection of the exciting and fluoresced x-ray beams, is seen to encompass portions of both coating layer 410 and bulk 420, such that the spectrum acquired of first inspection volume 570 will contain information about the elemental composition of both the coating layer and bulk material.

FIG. 5B depicts eclipser 510 moved (by operation of actuator 520) to a position that blocks portions of the exciting and fluoresced x-rays. The resultant second inspection volume 580 extends only through bulk 420, such that the spectrum acquired of second inspection volume 580 includes only information about the elemental composition of the bulk material. As discussed above, comparison of the spectra acquired from the first and second inspection volumes will indicate whether an element of interest is located only in the coating layer, only in the bulk, or in both.

While eclipser 510 is shown to block portions of exciting and fluoresced x-rays, certain implementations of the invention may utilize an eclipser that blocks only one of the exciting or fluoresced x-ray beams. Other implementations may utilize an eclipser comprised of multiple structures, in place of the single structure shown in FIGS. 5A and 5B.

Those skilled in the art will recognize that the methods disclosed herein for rapid lead concentration screening may be easily extended to screening for other elements (e.g., cadmium) that are detectable by XRF analysis and which are or may become subject to regulatory limits.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of inspecting a sample by x-ray fluorescence (XRF) analysis, comprising:
    irradiating a sample with a beam of exciting x-rays having energies suitable for causing an element of interest to emit characteristic fluorescent x-rays;
    detecting the fluorescent x-rays emitted from a first inspection volume located at least partially in the sample and measuring a first intensity of the detected fluorescent x-rays emitted from the first inspection volume;
    detecting the fluorescent x-rays emitted from a second inspection volume located at least partially in the sample and measuring a second intensity of the detected fluorescent x-rays emitted from the second inspection volume, wherein the first inspection volume overlaps with and is non-identical to the second inspection volume;
    comparing the first intensity to the second intensity; and
    determining a location of the element of interest based on the comparison.

2. The method of claim 1, further comprising a step of moving a collimator to between first and second positions to vary the collimation of the exciting x-rays.

3. The method of claim 1, further comprising a step of moving a collimator between first and second positions to vary the collimation of the exciting x-rays.

4. The method of claim 1, further comprising a step of moving an eclipser between first and second positions to vary the degree of blocking of the exciting and fluorescing x-rays.

5. The method of claim 1, wherein the first inspection volume extends to a coating layer portion and a bulk portion of the sample, and the second inspection volume extends only to a bulk portion of the sample.

6. The method of claim 1, further comprising a step of deriving a concentration of the element of interest in the determined location.

7. The method of claim 1, further comprising a step of comparing a ratio of the first to second intensities to an empirically derived calibration ratio.

8. The method of claim 1, wherein the element of interest is lead.

9. An XRF analyzer, comprising:
    an x-ray source for directing a beam of exciting x-rays onto a sample to cause an element of interest to emit characteristic fluorescent x-rays;
    a detector positioned to receive fluorescent x-rays from an inspection volume and to responsive produce detection signals;
    an actuator for controllably changing the inspection volume; and
    a programmable controller having logic for operating the actuator to define a first inspection volume, measuring a first intensity of the detected fluorescent x-rays emitted from the first inspection volume, operating the actuator to define a second inspection volume, measuring a second intensity of the detected fluorescent x-rays emitted from the second inspection volume, and comparing the first intensity to the second intensity to determine a location of the element of interest;
    wherein the first inspection volume overlaps with and is non-identical to the second inspection volume.

10. The XRF analyzer of claim 9, wherein the actuator is coupled to a collimator structure movable between first and second positions, and wherein moving the collimator structure between first and second positions varies the collimation of the exciting x-rays to thereby change the inspection volume.

11. The XRF analyzer of claim 9, wherein the actuator is coupled to a collimator structure movable between first and second positions, and wherein moving the collimator structure between first and second positions varies the collimation of the fluorescent x-rays to thereby change the inspection volume.

12. The XRF analyzer of claim 9, wherein the actuator is coupled to an eclipser structure movable between first and second positions, and wherein moving the eclipser structure between first and second positions varies a degree of blocking of the exciting x-rays and the fluorescent x-rays to thereby change the inspection volume.

* * * * *

UNITED STATES PATENT AND TRADEMARK OFFICE
CERTIFICATE OF CORRECTION

PATENT NO.       : 8,229,064 B2                                       Page 1 of 1
APPLICATION NO.  : 12/771646
DATED            : July 24, 2012
INVENTOR(S)      : Grodzins It is certified that error appears in the above-identified patent and that said Letters Patent is hereby corrected as shown below:

Col. 8, lines 20-23 in Claim 9, replace "a detector positioned to receive fluorescent x-rays from an inspection volume and to responsive produce detection signals;" with --a detector positioned to receive fluorescent x-rays from an inspection volume and in response produce detection signals;--

Signed and Sealed this
Sixth Day of November, 2012

David J. Kappos
*Director of the United States Patent and Trademark Office*